United States Patent [19]

Frost

[11] Patent Number: 5,168,056
[45] Date of Patent: Dec. 1, 1992

[54] ENHANCED PRODUCTION OF COMMON AROMATIC PATHWAY COMPOUNDS

[75] Inventor: John W. Frost, Lafayette, Ind.

[73] Assignee: Purdue Research Foundation, West Lafayette, Ind.

[21] Appl. No.: 652,933

[22] Filed: Feb. 8, 1991

[51] Int. Cl.⁵ .................. C12N 15/67; C12N 15/70; C12N 9/10; C12N 9/00

[52] U.S. Cl. ...................... 435/172.3; 435/183; 435/193; 435/320.1; 536/27

[58] Field of Search .............. 435/172.3, 183, 193, 435/320.1; 536/27

[56] References Cited

U.S. PATENT DOCUMENTS

| | | | |
|---|---|---|---|
| 3,970,522 | 7/1976 | Sasajima et al. | 435/105 |
| 4,681,852 | 7/1987 | Tribe | 435/108 |
| 4,753,883 | 6/1988 | Backman et al. | 435/232 |
| 4,908,312 | 3/1990 | Ozaki et al. | 435/108 |

OTHER PUBLICATIONS

A. J. Pittard, "Biosynthesis of the Aromatic Amino Acids", in *Escherichia coli & Salmonella typhimurium*, Editor in Chief: F. C. Neidhardt, American Soc. for Microbiology, Washington, pp. 368-394, 1987.

K. M. Herrmann et al., "The Common Aromatic Biosynthetic Pathway" in Amino Acids: Biosynthesis and Genetic Regulation, Addison-Wesley Reading, pp. 301-376, 1983.

K. M. Draths et al., "Synthesis Using Plasmid-Based Biocatalysis: Plasmid Assembly and 3-Deoxy-D-arabino-heptulosonate Production", JACS, vol. 112, pp. 1657-1659, 1990.

Primary Examiner—Richard A. Schwartz
Assistant Examiner—Philip W. Carter
Attorney, Agent, or Firm—Barnes & Thornburg

[57] ABSTRACT

A genetic element comprising an expression vector and a gene coding for transketolase is utilized to enhance diversion of carbon resources into the common aromatic pathway.

19 Claims, 3 Drawing Sheets

FIG. 6

ENHANCED PRODUCTION OF COMMON AROMATIC PATHWAY COMPOUNDS

BACKGROUND AND SUMMARY OF THE INVENTION

This invention relates to the enhancement of whole cell biosynthesis of precursors of chorismate and compounds biosynthetically derived therefrom. More particularly, this invention relates to overproduction in whole cells of enzymes that catalyze the biosynthetic production of aromatic compounds.

Chorismate is an intermediate in biosynthetic pathways that lead to the production of aromatic compounds such as phenylalanine, tryptophan, tyrosine, folate, melanin, ubiquinone, menaquinone, prephenic acid (used in the production of the antibiotic bacilysin) and enterochelin. Because of the large number of biosynthetic pathways that depend from chorismate, the biosynthetic pathway utilized by organisms to produce chorismate is often known as the "common aromatic pathway". The common aromatic pathway (sometimes referred to as the "shikimate pathway" because shikimate was the first identified intermediate in the pathway) is generally considered to begin with the DAHP-synthase catalyzed condensation of the precursor compounds erythrose 4-phosphate and phosphoenolpyruvate to form 3-Deoxy-D-arabino-heptulosonate 7-phosphate (DAHP) and . to end with the production of chorismate.

Efficient and cost-effective biosynthetic production of chorismate and its biosynthetic derivatives require that carbon sources such as glucose, lactose, galactose, or other sugars be converted to the desired product with high percentage yields. Accordingly, it is valuable from the standpoint of industrial biosynthetic production of aromatic compounds or other biosynthetic derivatives of chorismate to increase the influx of carbon sources into and through the common aromatic pathway thereby enhancing whole cell biosynthesis of chorismate and its derivatives.

The present invention provides for the enhanced commitment of cellular carbon sources to enter and flow through the common aromatic pathway by transferring into host cells genetic elements comprising a tkt gene and optionally other genetic elements encoding enzymes that direct carbon flow into or through the common aromatic pathway. The genetic elements can be in the form of extrachromosomal plasmids, cosmids, phages, or other replicons capable of carrying at least the gene tkt for expression in a host cell. The tkt gene codes for the enzyme transketolase, which catalyzes the conversion of carbon source D-fructose 6-phosphate to D-erythrose 4-phosphate, a necessary precursor compound for the common aromatic pathway. Overproduction of transketolase in tkt transformed cells has been found to provide an increased flow of carbon resources into the common aromatic pathway relative to carbon resource utilization in whole cells that do not harbor such genetic elements.

In addition to transketolase, other enzymes that catalyze steps of the common aromatic pathway or that catalyze production of compounds input into the common aromatic pathway can be overexpressed in whole cells to increase the efficiency of carbon conversion and biosynthetic throughput of the common aromatic pathway. The present invention also provides for transfer of genetic elements comprising the tkt gene, the gene coding for DAHP synthase (aroF in *E. coli*), an enzyme required for condensation of phophoenolpyruvate and erythrose 4-phosphate, the gene coding for 3-dehydroquinate synthase (aroB in *E. coli*), or other genes encoding enzymes that catalyze reactions in the common aromatic pathway. In a preferred aspect of the invention, an enzyme that produces a precursor to compounds input into the common aromatic pathway (such as transketolase) as well as one or more enzymes that catalyze biosynthetic steps of the common aromatic pathway are encoded on one or more plasmids transferred into a host cell. As a result of this transfer of genetic element(s), more carbon enters and moves through the common aromatic pathway relative to wild type whole cells not containing the genetic elements of the present invention.

Generally, the present invention enhances expression in a host cell of transketolase and other enzymes catalyzing conversion of substrates in the common aromatic pathway relative to wild type host cell expression of the enzymes. This enhanced expression of genes encoding the enzymes is attained either by the transfer and stable incorporation of extrachromosomal genetic elements into the host cell or by the transfer of the genetic elements into the genome of the host cell. The expressed gene products are enzymes configured to provide appropriate catalytic sites for substrate conversion of common aromatic pathway compounds.

DETAILED DESCRIPTION OF THE INVENTION

Figure 6:
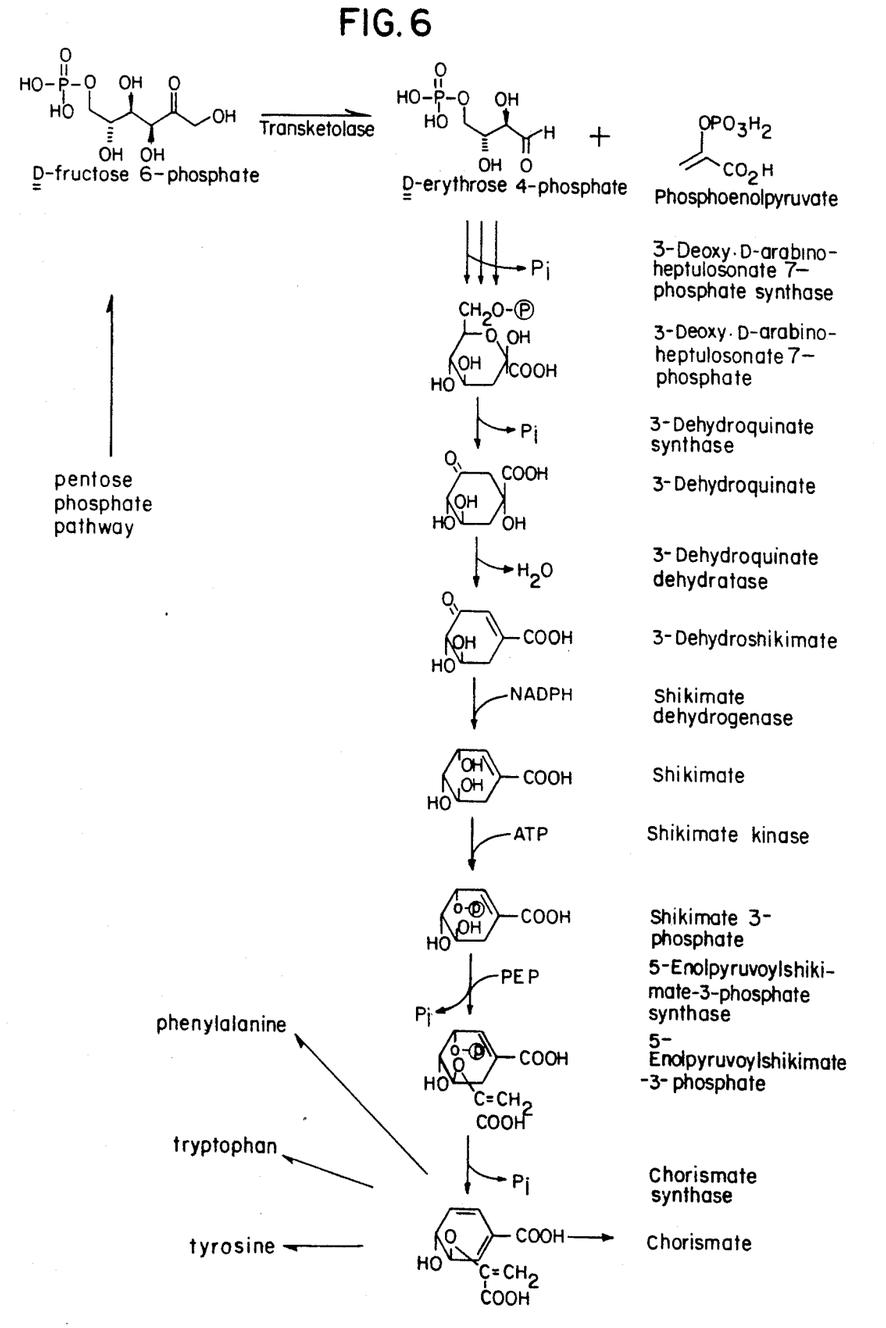
FIG. 6 depicts the common aromatic pathway and its relationship to other selected biosynthesis pathways.

With reference to FIG. 6, Scheme I, D-erythrose 4-phosphate, a precursor compound of the common aromatic pathway is an end product of the pentose phosphate pathway. The pentose phosphate pathway is situated between glycolysis and a variety of different biosynthetic cascades, and provides D-erythrose 4-phosphate from the pathway's non-oxidative branch as the carbon source to the common aromatic pathway. The nonoxidative pentose phosphate pathway converts D-fructose 6-phosphate into varying equivalents D-ribose 5-phosphate, D-sedoheptulose 7-phosphate, and D-erythrose 4-phosphate which are required, respectively, for the biosynthesis of nucleotides, gram-negative bacterial lipopolysaccharides, and compounds such as the aromatic amino acids phenylalanine, tyrosine, and tryptophan derived from the common aromatic biosynthetic pathway. Nonoxidative pentose phosphate pathway interconversion between D-fructose 6-phosphate and pentoses allows organisms such as *E. coli* to use the pentoses D-ribose, D-xylose, and D-arabinose as exclusive sources of carbon during growth.

The initial siphoning of intermediates from glycolysis by the pentose phosphate pathway involves transketolase catalyzed transfer of a ketol group from D-fructose 6-phosphate to D-glyceraldehyde 3-phosphate to form D-erythrose 4-phosphate and D-xylulose 5-phosphate. Pentose phosphate epimerase catalyzes conversion of the D-xylulose 5-phosphate into D-ribulose 5-phosphate followed by pentose phosphate isomerase mediated transformation of the D-ribulose 5-phosphate into D-ribose 5-phosphate. At this stage, the D-ribose 5-phosphate can be exploited by transketolase as an acceptor of a ketol group derived from another molecule of D-fructose 6-phosphate forming a second molecule of D-erythrose 4-phosphate and D-sedoheptulose 7-phosphate. Finally, the enzyme transaldolase catalyzes transfer of a dihydroxyacetone group from the D-sedoheptulose 7-phosphate to D-glyceraldehyde 3-phosphate yielding the third molecule of D-erythrose 4-phosphate and D-fructose 6-phosphate. A net conversion of two molecules of D-fructose 6-phosphate into three molecules of D-erythrose 4-phosphate is thus achieved by the nonoxidative pentose phosphate pathway.

The first committed step of the common aromatic pathway in the condensation of erythrose 4-phosphate produced by transketolase catalyzed conversion of carbon sources directed through the transketolase catalyzed portions of the pentose phosphate pathway. This is an aldol condensation between an intermediate carbanion of C-3 of phosphoenolpyruvate and the carbonyl C-1 of erythrose-4-phosphate. The majority of the Phosphoenolpyruvate molecules react stereospecifically with respect to the configuration on C-3, excluding he formation of a freely rotating intermediate methyl group.

The condensation of phosphoenolpyruvate and erythrose 4-phosphate is catalyzed by the enzyme DAHP synthase. Wild-type *E. coli* produces three DAHP synthase isoenzymes: phenylalanine-sensitive DAHP synthase (phe), tyrosine-sensitive DAHP synthase (tyr), and tryptophan-sensitive DAHP synthase (trp). The tetrameric DAHP synthase (phe) has a subunit molecular weight of 35,000, and the dimeric DAHP synthase (tyr) and DAHP synthase (trp) have subunit molecular weights approaching 40,000. The native forms of the enzymes are probably protein-phosphoenolpyruvate adducts. In *E. coli* the structural genes for DAHP synthase (tyr), DAHP synthase (phe), and DAHP synthase (trp) are aroF, aroG, and aroH, respectively, with gene locations at 56, 17, and 37 min on the *E. coli* linkage map. In wild-type *E. coli*, 80% of the total DAHP synthase activity is contributed by the phenylalanine-sensitive isoenzyme, and 20% is contributed by the tyrosine-sensitive isoenzyme. There are only traces of the DAHP synthase (trp) in *E. coli*.

After the committed step, the next reaction of the common aromatic pathway is an intramolecular exchange of the DAHP ring oxygen with C-7, accompanied by an oxidation at C-6 and a reduction at C-2. Cleavage of the phosphoester provides the driving force to form 3-dehydroquinate (DAH).

The reaction is catalyzed by dehydroquinate synthase (DAH synthase). Pure DAH synthase from *E. coli* is a single polypeptide chain having a molecular weight of 40–44,000. The enzyme requires Co and NAD for activity, the latter in catalytic amounts. The formation of 3-dehydroquinate from DAHP is stereospecific and occurs with inversion of the conformation on C-7 of DAHP without exchange of hydrogen with the growth medium.

A stereospecific syn-dehydration of 3-dehydroquinate introduces the first double bond of the aromatic ring system to yield 3-dehydroshikimate. The reaction is catalyzed by 3-dehydroquinate dehydratase. Schiff base formation between enzyme and substrate causes a conformational change in the substrate (twisted boat) that leads to the stereospecific course of the reaction.

Shikimate biosynthesis from 3-dehydroshikimate is catalyzed by shikimate dehydrogenase. This NADP-specific enzyme facilitates the hydrogen transfer from the A-side of NADPH.

Shikimate is phosphorylated to shikimate 3-phosphate by shikimate kinase. The shikimate kinase is a polypeptide of 10,000 daltons that is complexed with the bifunctional DAHP synthase-chorismate mutase. The kinase, only active in the complex, has been purified to homogeneity. Since the enzyme is inhibited by chorismate, prephenate, ADP, and 5-enolpyruvoylshikimate 3-phosphate and derepressed by growth on limiting tyrosine, shikimate kinase is believed to represent a key allosteric control point of the pathway in some types of host cells.

Shikimate 3-phosphate reacts with phosphoenolpyruvate to form 5-enolpyruvoylshikimate 3-phosphate and inorganic phosphate. The reversible enzyme-catalyzed reaction is a transfer of an unchanged enolpyruvoyl moiety of phosphoenolpyruvate. Protonation of C-3 of phosphoenolpyruvate combined with a nucleophilic attack of the 5-hydroxyl of shikimate leads to a presumed intermediate from which 5-enolpyruvoylshikimate 3-phosphate is obtained in a 1,2-elimination of orthophosphate. The reaction is catalyzed by 5-enolpyruvoylshikimate 3-phosphate synthase.

The second double bond in the aromatic ring system is introduced through a trans-1,4-elimination of orthophosphate from 5-enolpyruvoylshikimate 3-phosphate to yield chorismate. The reaction is catalyzed by chorismate synthase.

From the key intermediate chorismate, the endpoint of the common aromatic pathway, biosynthesis of a diverse number of aromatic compounds is possible. For example, as indicated in Scheme I, the aromatic amino acids tryptophan, tyrosine, and phenylalanine can be synthesized from chorismate along their respective biosynthetic pathways. As previously noted, other commercially important aromatic compounds also produced from chorismate include folates, aspartame, melanin, and prephenic acid.

The present invention encompasses modification of a host cell to cause overexpression of substrates and/or overexpression or derepression of enzymes acting in the pentose phosphate or common aromatic pathway in conjunction with the overexpression of an enzyme having the catalytic properties of naturally derived transketolase. Enzymes having the catalytic activity of transketolase include but are not limited to transketolase produced by expression in whole cells of a naturally derived transketolase gene, enzymes produced by expression in whole cells of a naturally derived transketolase gene modified by sequence deletion or addition so that the expressed enzyme has an amino acid sequence that varies from unmodified transketolase, abzymes produced to have catalytic sites with steric and electronic properties corresponding to catalytic sites of transketolase, or other proteins produced to have the capability of catalyzing the conversion of D-fructose 6-phosphate to erythrose 4-phosphate by any other art recognized means. Enzymes catalyzing reactions in the pentose phosphate or common aromatic pathway include those enzymes produced by expression in whole cells of naturally derived pentose phosphate or common aromatic pathway genes, enzymes produced by expression of naturally derived pentose phosphate or common aromatic pathway genes that have been modified by sequence deletion or addition so that the expressed enzyme has an amino acid sequence that differs from the natural enzyme, or abzymes having catalytic sites with steric and electronic properties corresponding to catalytic sites of a natural enzyme in the common aromatic or pentose phosphate pathway.

Transketolase or enzymes having transketolase-like catalytic activity can be overexpressed relative to transketolase production in wild type cells (as measured by standard transketolase activity assays known in the art and described in Example 1) in conjunction with any number of other enzymes in the common aromatic pathway. For example, overexpression of both transketolase and DAHP synthase, transketolase and DHQ synthase, transketolase and DAHP synthase and DHQ synthase, transketolase and shikimate kinase, transketolase and chorismate mutase, or any other common aromatic pathway enzymes in conjunction with transketolose overproduction can enhance carbon source input and/or throughput of the common aromatic pathway.

Enhanced expression of genes coding for proteins able to perform or control pentose phosphate or common aromatic pathway enzymatic functions is mediated by genetic elements transferable into a host cell. Genetic elements as herein defined include nucleic acids (generally DNA or RNA) having expressible coding sequences for products such as proteins, apoproteins, or antisense RNA, which can perform or control pentose phosphate or common aromatic pathway enzymatic functions. The expressed proteins can function as enzymes, repress or derepress enzyme activity, or control expression of enzymes. The nucleic acids coding these expressible sequences can be either chromosomal (e.g. integrated into a host cell chromosome by homologous recombination) or extrachromosomal (e.g. carried by plasmids, cosmids, etc.). In addition, genetic elements are defined to include optional expression control sequences including promotors, repressors, and enhancers that act to control expression or derepression of coding sequences for proteins, apoproteins, or antisense RNA. For example, such control sequences can be inserted into wild type host cells to promote overexpression of selected enzymes already encoded in the host cell genome, or alternatively can be used to control synthesis of extrachromosomally encoded enzymes.

The genetic elements of the present invention can be introduced into a host cell by plasmids, cosmids, phages, Yeast artificial chromosomes or other vectors that mediate transfer of the genetic elements into a host cell. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements in accordance with the present invention have been inserted. Plasmid borne introduction of the genetic element into host cells involves an initial cleaving of a plasmid with a restriction enzyme, followed by ligation of the plasmid and genetic elements in accordance with the invention. Upon recircularization of the ligated recombinant plasmid, transduction (e.g., P1 transduction process) or other mechanism for plasmid transfer (e.g. electroporation, microinjection, etc.) is utilized to transfer the plasmid into the host cell. Plasmids suitable for insertion of genetic elements into the host cell include but are not limited to pBR322 and its derivatives such as pAT153, pXf3, pBR325, and PBR327, pUC vectors, pACYC and its derivatives, pSC101 and its derivatives, and ColE1.

Suitable host cells for use in the present invention are members of those genera capable of being utilized for industrial biosynthetic production of desired aromatic compounds. Accordingly, host cells can include prokaryotes belonging to the genera Escherichia, Corynebacterium, Brevibacterium, Arthrobacter, Bacillus, Pseudomonas, Streptomyces, Staphylococcus, or Serratia. Eukaryotic host cells can also be utilized, with yeasts of the genus Saccharomyces or Schizosaccharomyces being preferred.

More specifically, prokaryotic host cells are derived from species that include *Escherichia coli, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor Streptomyces griseus, Streptomyces kasugensis, Streptomyces lavendulae, Streptomyces lipmanii, Streptomyces lividans, Staphylococcus epidermis, Staphylococcus saprophyticus,* or *Serratia marcescens.* Preferred eukaryotic host cells include *Saccharomyces cerevisiae* or *Saccharomyces carlsbergensis.*

For industrial production of primary metabolites derived from chorismate (such as aromatic amino acids), deregulated mutant strains of the above recited species that lack feedback inhibition of one or more enzymes in the metabolic biosynthetic pathway are preferred. Such strains can be created by random or directed mutagenesis, or are commercially available. Examples of *E. coli* strains having DAHP synthase, prephenate dehydratase, or chorismate mutase feedback inhibition removed are described in U.S. Pat. No. 4,681,852 to Tribe and U.S. Pat. No. 4,753,883 to Backman et al.

In preferred embodiments, the present invention is a method for increasing carbon flow into the common aromatic pathway of a host cell. Increasing carbon flow requires the step of transforming the host cell with recombinant DNA containing a tkt gene so that transketolase is expressed at enhanced levels relative to wild type host cells. Co-overexpression of other enzymes of the common aromatic pathway require the additional step of transferring into the host cell one or more genes coding for enzyme(s) catalyzing reactions in the common aromatic pathway. The genes transferred can be selected from the group consisting of the DAHP synthase gene and DHQ synthase gene (preferably the aroF or aroB genes respectively). The preferred host cell is a strain of E. coli such as BJ502 aroB.

Another preferred embodiment of the present invention is a method for enhancing a host cell's biosynthetic production of compounds derived from the common aromatic pathway (via the chorismate intermediate, see Scheme I). This method involves the step of increasing expression of transketolase in the host cell relative to a wild type host cell. The step of increasing expression of transketolase can include transferring into the host cell a vector carrying the tkt gene.

In another embodiment of the present invention, a method for enhancing a host cell's biosynthetic production of compounds derived from the common aromatic pathway relative to wild type host cell's biosynthetic production of such compound is provided. This method requires the step of increasing expression in a host cell of a protein catalyzing conversion of D-fructose 6-phosphate to erythrose 4-phosphate. The expression of such a protein can involve transferring into the host cell a tkt gene.

In other preferred embodiments, the present invention is a genetic element comprising the tkt gene and a gene selected from the group consisting of the aroF gene and the aroB gene. Plasmid pKD130A is an example of a vector carrying the genetic elements coding for transketolase and DAHP synthase.

Another embodiment is provided by DNA that includes a vector carrying a gene coding for transketolase. The vector can be plasmid pBR325, and optionally a gene coding for DAHP synthase can also be carried on the vector. Plasmid KD130A is an example wherein the gene coding for transketolase and the gene coding for DAHP synthase are both carried on the same pBR325 vector.

Yet another embodiment of the invention is provided by plasmid pKD112A, which consists of a plasmid vector carrying a tkt gene. Substantially pure E. coli transketolase can be isolated from cells harboring the pKD112A plasmid.

The following list of abbreviations for compounds commonly noted in the specification and Examples is presented as follows:

| | |
|---|---|
| DHQ | 3-dehydroquinate |
| DAH | 3-deoxy-D-arabino-heptulosonic acid |
| DAHP | 3-deoxy-D-arabino-heptulosonic acid 7-phosphate |
| TSP | 3-(trimethylsilyl)propionic-2,2,3,3-$d_4$ acid, sodium salt |
| PEP | phosphoenolpyruvate |
| NADH | β-nicotinamide adenine dinucleotide phosphate, reduced form |
| Kan | kanamycin |
| Ap | ampicillin |
| Tc | tetracycline |
| Cm | chloramphenicol |

EXAMPLE 1

A genetic element which encodes transketolase was found in an *Escherichia coli* K-12 genomic library. This isolated locus (tkt) was used to vary the specific activity of transketolase in *E. coli* aroB. a strain which accumulates 3-deoxy-D-arabino-heptulosonate (DAH). Variations in transketolase specific activity were found to have significant impact on the flow of carbon directed into aromatic amino acid biosynthesis as measured by the accumulation of DAH.

EXPERIMENTAL PROCEDURES

Culture Medium All growth solutions were prepared in distilled, deionized water. LB medium contained Bacto tryptone (10 g), Bacto yeast extract (5 g), and sodium chloride (10 g) in 1 L of water. M9 medium contained $Na_2HPO_4$ (6 g), $KH_2PO_4$ (3 g), NaCl (0.5g), $NH_4Cl$ (1 g), $MgSO_4$ (0.12 g), thiamine (1 mg), and shikimic acid (40 mg) where indicated. Unless otherwise specified, the carbon source in M9 was glucose. Other carbon sources included either D-arabinose, D-ribose, or D-xylose. M9 solid and liquid medium contained, respectively 4 g and 2.5 g of carbon source per liter of medium. During optimization of the whole cell synthesis, glucose concentrations of 2.5 g, 5.0 g, 10 g, and 30 g per liter of M9 liquid medium were examined. M63 medium in 1 L, contained $KH_2PO_4$ (13 6 g), $(NH_4)_2SO_4$ (2 g), $FeSO_4 \cdot 7H_2O$ (0.5 mg), D-glucose (2 g), $MgSO_4$ (0.12 g), thiamine (1 mg) and was supplemented with L-proline (40 mg), L-arginine (40 mg), L-histidine (40 mg), L-valine (40 mg), and L-isoleucine (40 mg). This medium was additionally supplemented, where required, with shikimic acid (120 mg). Ampicillin (50 mg/L), chloramphenicol (34 mg/L), kanamycin (50 mg/L), and tetracycline (12.5 mg/L) were added to growth solutions as appropriate. Solutions of inorganic salts, magnesium salts, and carbon sources were autoclaved separately and then mixed. Antibiotics, thiamine, amino acids, and shikimic acid were introduced by syringe through sterilizing 0.2 micron membranes (Nalgene). Agar (1.5% weight to volume) plates were prepared with either Difco agar for LB medium or from agarose (Type II, medium EE0, Sigma) for minimal plates.

Assays for Protein, DAH/DAHP, Glucose, Transketolase, and DAHP Synthase. Protein was assayed using the Bradford dye-binding procedure with protein assay solution purchased from Bio-Rad. A standard curve was prepared using bovine serum albumin. DAH and DAHP concentrations were determined by thiobarbituric acid visualization of the periodate cleavage products. This assay was suitable for measuring relative concentrations of DAH and DAHP. For measurement of the absolute concentrations of DAH and DAHP present, $^1H$ NMR analysis was used. A measured aliquot was withdrawn from the accumulation supernatant and concentrated. Deuterated water (99.8%) was added followed by concentration. The residue was dissolved in a known volume of deuterated water (99.8%) containing a quantitated amount of 3-(trimethylsilyl)-propionic-2,2,3,3-$d_4$ acid, sodium salt (TSP). Concentrations of DAH and DAHP were then determined by integration of the $^1H$ NMR resonances of the 3-deoxy (DAH and DAHP) and TSP protons.

Transketolase activity was assayed in either of two ways. In the first method the assay solution (1 mL) contained triethanolamine buffer (150 mM), pH 7.6, $MgCl_2$ (5 mM), thiamine pyrophosphate (0.1 mM), NADP (0.4 mM), β-hydroxypyruvate (0.4 mM), D-erythrose 4-phosphate (0.1 mM), glucose 6-phosphate dehydrogenase (3 units), and phosphoglucose isomerase (10 units). The D-erythrose 4-phosphate was prepared from D-glucose 6-phosphate. After incubation for five min to allow any glucose 6-phosphate to react, enzyme solution was added and the reaction monitored at 340 nm for 20-30 min. Absorbance at 340 nm was monitored with one unit of activity defined as the formation of 1 micromole of NADPH per min.

A second assay method for transketolase activity used an assay solution (1 mL) containing (final concentration) potassium 3-(N-morpholino)propanesulfonate buffer (200 mM), pH 7.5, ribose 5-phosphate (2 mM), D-ribulose 5-phosphate 3-epimerase (1 unit) and phosphoriboisomerase (3 units) was incubated at 25° C. for 15 min. NADH (0.5 mM), thiamine pyrophosphate (0.1 mM), $MgCl_2$ (0.1 mM), $AsO_4$ (25 mM) and glyceraldehyde 3-phosphate dehydrogenase (5 units) were then added followed by the transketolase-containing solution. Absorbance at 340 nm was monitored continuously with one unit of transketolase activity defined as the loss of 1 micromole of NADH per min.

Phosphoenolpyruvate and D-erythrose 4-phosphate required for the assay of DAHP synthase activity were synthesized according to literature procedure. DAHP synthase was assayed by preparing two different solutions and incubating them separately at 37° C. for 10 min. The first solution (1 mL) contained potassium phosphate buffer (250 mM), pH 7, phosphoenolpyruvate (12.5 mM), D-erythrose 4-phosphate (6.5 mM) and ovalbumin (1 mg). The second solution (0.5 mL) consisted of the DAHP synthase-containing sample diluted in potassium phosphate (50 mM), pH 7, phosphoenolpyruvate (0.5 mM) and 1,3-propanediol (250 mM). After the two solutions were mixed, 0.15 mL aliquots were withdrawn at timed intervals and quenched by addition of 0.10 mL of 10% trichloroacetic acid. Precipitated protein was separated by centrifugation and the DAHP in the supernatant measured by thiobarbiturate assay. One unit of DAHP synthase activity is defined by the catalyzed formation of 1 micromole of DAHP per minute.

Purification of *E. coli* Transketolase. Frozen *E. coli* K-12 used for the transketolase purification was purchased from Grain Processing, Inc., Muscatine, Iowa. Bio-Rad hydroxylapatite, Whatman diethylaminoethyl cellulose DE52, and a 7.5 mm × 7.5 cm DEAE-5PW TSK analytical (purchased from Beckman) HPLC column were used during the purification. HPLC purification utilized a Waters system (U6K injector, Model 510 pumps, Model 680 gradient controller, and an extended wavelength module). Buffers used during transketolase purification included buffer A: potassium phosphate (50 mM), $MgCl_2$ (1 mM), dithiothreitol (0.2 mM), pH 7.35; buffer B: potassium Phosphate (250 mM), $MgCl_2$ (1 mM), dithiothreitol (0.2 mM), pH 7.35; buffer C: potassium phosphate (10 mM), $MgCl_22$ (1 mM), pH 7.35; buffer D: potassium phosphate (10 mM), $MgCl_2$ (1 mM) and KCl (500 mM), pH 7.35; and buffer E: potassium phosphate (250 mM), $MgCl_2$ (1 mM), pH 7.35. Unless otherwise specified, all protein manipulations were carried out at 40° C. and buffered solutions were maintained at 40° C. Protein solutions were concentrated by ultrafiltration (PM-10 Diaflo membranes from Amicon).

Frozen cell paste (18 g) of *E. coli* K-12 was thawed in 45 mL of buffer A. The cells were then lysed by two passes through a French press at 16000 psi. Cell debris was removed by centrifugation at 18000 g for 20 min. A slurry of hydroxylapatite in 30 mL of buffer A was added, the mixture centrifuged at 18000 g for 20 min. and the supernatant then saved. The pellet was resuspended in 30 mL buffer A, centrifugation repeated at 18000 g for 7 min, and the resulting supernatant saved. The two supernatants were combined and applied to a column of DEAE-cellulose (110 mL) which had been preequilibrated with buffer A. Elution with buffer A (110 mL) vas followed by elution with a linear gradient (500 mL + 500 mL, buffer A—buffer B). Fractions containing transketolase were concentrated. Further purification utilized high pressure liquid chromatography on a DEAE column. Transketolase-containing solutions were applied to the HPLC column which had been preequilibrated (77:23 buffer C/buffer D). Transketolase was then eluted with a linear gradient (77:23 buffer C/buffer D—68:32 buffer C/buffer D). Fractions containing transketolase activity were concentrated, desalted using buffer C, and then purified by HPLC once again. The second HPLC separation began with application of the protein to a preequilibrated (70:30 buffer C/buffer E) HPLC DEAE column. Transketolase was eluted with a linear gradient (70:30 buffer C/buffer E—50:50 buffer C/buffer E). Active fractions were concentrated, quick frozen in liquid nitrogen, and stored at 70° C.

Polyacrylamide gel electrophoresis of purified transketolase was performed in the presence of sodium dodecyl sulfate (SDS). The stacking gel was buffered with Tris HCl at pH 6.8., and the separating gel (12.5% acrylamide) was buffered with Tris HCl at pH 8.8. Typically, 30 micrograms of protein were loaded per lane. Gels were fixed with acetic acid solution and visualized with Coomassie Brilliant Blue. Standards used for molecular weight determination were purchased from Sigma and included lysozyme (14300), p-lactoglobulin (18400), ovalbumin (43000), bovine serum albumin (68000), phosphorylase B (97000), and myosin-H chain (200000). Log $M_r$ was plotted against $R_f$ for the standards to give the standard curve needed to determine transketolase's $M_r$. Crosslinking of purified transketolase entailed the reaction (in a total volume of 0.05 mL) of transketolase (0.5 mg/mL) with dimethyl suberimidate (0-10 mg/mL) in 0.2M borate, pH 9.5, for 3 hr at 25° C. Addition of 10% sodium dodecyl sulfate (0.005 mL) and β-mercaptoethanol (0.0005 mL) was followed by incubation at 37° C. for 2 h. Polyacrylamide gel electrophoresis was used to separate the transketolase. The separating gel (5% acrylamide) was buffered with 0.1M sodium borate and 0.1M sodium acetate, pH 8.5 and contained sodium dodecyl sulfate (0.1%). Gels were fixed and stained as previously described.

Genetic Manipulations

All restriction enzymes, T4 DNA ligase, T4 kinase, mung bean nuclease, and EcoRI linker oligonucleotide (5'-CCGAATTCGG) were obtained from Bethesda Research Laboratories. Calf intestinal alkaline phosphatase was obtained from Pharmacia.

Host Construction *E. coli* BJ502 was made aroB by P1 transduction from JB5 (aroB malT::Tn5). Selection of transductants for $Kan^R$ followed by screening for lack of growth on M9/glucose and growth on M9/glucose supplemented with shikimate yielded a number of BJ502 aroB candidates. These candidates were then transformed with pKD44B and assayed for accumulation of DAH and DAHP in the growth supernatant in order to isolate BJ502 aroB strains.

Wild-type transketolase activity was restored to BJ502 by P1 transduction of the tkt locus from *E. coli* RB791. Transductants were initially selected for the ability to grow on M9/ribose plates. Subsequent selection for the ability to grow on M9/glucose, M9/arabinose, and M9/xylose yielded *E. coli* BJ502 tkt+. An aroB mutation was introduced into BJ502 tkt+ by P1 transduction of the mutated locus from *E. coli* J85. Selection of transductants for Kan$^R$ was followed by screening for lack of growth on M9/glucose and growth when cultured on M9/glucose/shikimate plates.

tkt Isolation Chromosomal DNA purified from *E. coli* RB791 was partially digested with BamHI under conditions of high enzyme concentration for short periods of time. The resulting 20–30 kb fragments were ligated by treatment with T4 DNA ligase into cosmid pLAFR3 which had previously been digested with BamHI and then treated with alkaline phosphatase. Cosmids containing the genomic inserts were added to freshly prepared lambda extract for incorporation into phage heads. Infection of *E. coli* BJ502 with the library produced 50000 Tc$^R$ transformants per mL of extract. Transformants were selected for the ability to grow on pentose plates and glucose plates lacking aromatic supplementation. The tkt mutation of BJ502 was complemented by 18 cosmids which were isolated and restriction enzyme mapped with BamHI, PstI, SalI, and EcoRI. Of the cosmids, 14 of 18 gave the identical number and size of fragments after digestion with the aforementioned restriction enzymes. The cosmid yielding this common restriction enzyme map was designated p10. Restriction enzyme digest of p10 with BamHI provided four fragments which were isolated and individually introduced into pLAFR3. The resulting cosmids were transformed into BJ502. Selection for complementation of the tkt mutation indicated that the transketolase gene was localized in a 5 kb insert. The cosmid containing the 5 kb tkt containing insert was designated pKD44B.

Plasmid Constructions. (pKD116B) Plasmid pKB945 which contains the aroF gene encoded on a 6 kb fragment was digested with BamHI and HindIII. Restriction fragments were ligated into pBR322 which had been previously digested with BamHI and HindIII. One of the resulting plasmids, pAROF3 contained a 2.4 kb BamHI-HindIII fragment which was able to complement the DAHP synthase mutane *E. coli* AB3248 when cultured in M63 medium. *E. coli* AB3248 lacks all isozymes of DAHP synthase. Plasmid pAROF3 was digested with EcoRI and BamHI, treated with mung bean nuclease, and EcoRI linker oligonucleotides ligated to the resulting blunt ends. Following digestion with EcoRI, DNA fragments were separated on an agarose gel (0.7%) and the band at 2.4 kb excised and purified. The fragment was ligated into pBR325 which had previously been digested with EcoRI followed by treatment with alkaline phosphatase. The resulting plasmid was transformed into DH5α. Plasmids were purified by the alkaline lysis method from transformants which were Ap$^R$, Tc$^R$, and Cm$^S$. The resulting plasmid, pKD116B, contained a 2.4 kb EcoRI insert and was able to complement *E. coli* AB3248 cultured on M63 medium.

(pKD112A) Plasmid pKD44B was digested with BamHI and the resulting fragments ligated into pBR325 which had been previously digested with BamHI followed by alkaline phosphatase. Plasmids were then introduced into DH5α and transformants selected for Ap$^R$, Tc$^S$, and Cm$^R$. Restriction enzyme analysis of the purified plasmids resulted in the isolation of pKD112A which contains the 5 kb fragment containing tkt. Plasmid pKD112A complemented the tkt mutation of BJ502.

(pKD130A) Plasmid pKD116B was digested with BamHI, treated with alkaline phosphatase and ligated to an insert resulting from BamHI digestion of pKD44B. Transformation into DH5α, selection for Ap$^R$, Tc$^S$, and Cm$^S$ colonies, followed by plasmid purification resulted in the isolation of pKD130A. Separation of the fragments generated from restriction enzyme digestions with BamHI, SalI, and EcoRI confirmed the presence of both the 2.4 kb aroF insert as well as the 5 kb tkt insert. Plasmid pKD130A complemented the DAHP synthase mutant AB3248 cultured on M63 medium but failed to complement the tkt mutant BJ502.

(pKD272A) and (pKD272B) Plasmid pKD116B was digested with EcoRI and ligated with PLAFR3 which had been previously digested with EcoRI followed by alkaline Phosphatase. Cosmids were transformed into DH5α. Plasmid DNA was purified from transformants and resulted in the isolation of plasmids pKD272A and pKD272B, both of which contained the 2.4 kb aroF-encoding fragment. Plasmids pKD272A and pKD272B differ from each other only in the orientation of the insert with respect to the vector. Both pKD272A and pKD272B complement *E. coli* AB3248 grown on M63 medium.

Figure 4:
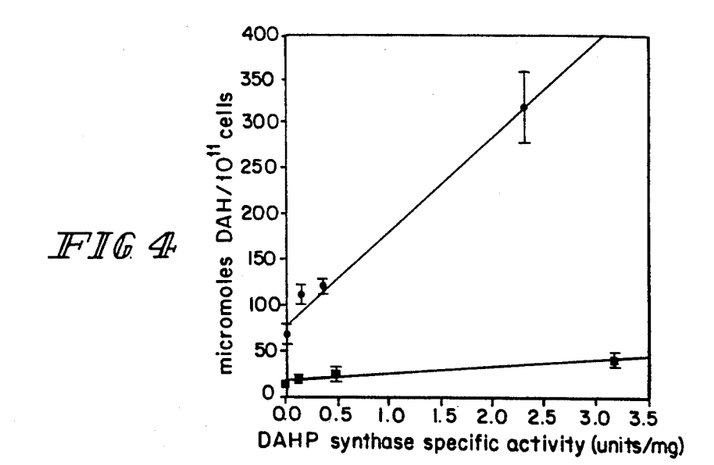
FIG. 4 illustrates the impact on DAH/DAHP synthesis arising from incremental increases of DAHP synthase activity on transketolase activity at wild-type transketolase levels in BJ502 tkt+ aroB (●) and depleted transketolase levels in BJ502 aroB (■)

Cell Growth, Cell Density, DAH/DAHP Concentration, and Transketolase/DAHP synthase Specific Activities Used for FIG. 4. A fresh colony was used to inoculate a culture tube (15×180 mm) containing 5 mL of LB with the appropriate antibiotic. Cells were grown for 12 hr at 37° C. with aeration. Cells were collected and resuspended in a second culture tube containing 5 mL of M9 glucose medium supplemented with shikimic acid and the appropriate antibiotic. After 48 hr of incubation at 37° C., cell concentration was measured by the optical density at 600 nm ($8 \times 10^8$ cells/mL = 1 OD). An aliquot was withdrawn and saved. All DAH/DAHP concentrations were determined at the same time by the thiobarbiturate assay.

Determination of transketolase specific activities began with growth of cells in four 4 L Erlenmeyer flasks each of which contained 2 L of LB medium along with the appropriate antibiotic. A 1% inoculant of a fresh culture was used to inoculate the growths followed by incubation at 37° C. for 9 hr. Cells were harvested by centrifugation at 10000 g for 7 min at 4° C. Cell paste (approximately 18 g) was suspended in 40 mL of cold buffer A as described for the transketolase purification. Transketolase was purified up to but not inclusive of the HPLC DEAE column.

DAHP synthase specific activity determinations began with addition of a 1% inoculant to 1 L of medium containing the appropriate antibiotic in a 4 L Erlenmeyer. Cells were grown to late log phase (7-8 hr). After being harvested by centrifugation at 10000 g for 5 min at 4° C., cells were resuspended in 50 mM potassium phosphate, pH 7, containing phosphoenolpyruvate (10 mM) and CoCl$_2$ (0.05 mM). Cells were lysed by two passes through a French press at 18000 psi, cellular debris removed by centrifugation at 25000 g for 30 min at 4° C., and DAHP synthase activity determined as previously described.

Figure 2:
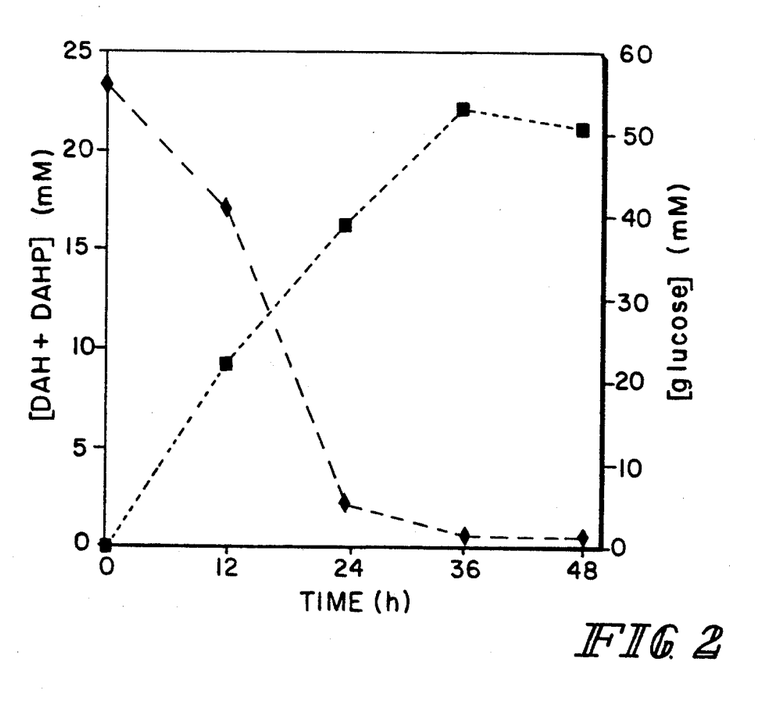
FIG. 2 is a graphical representation of concentration changes in D-glucose (♦) and DAH/DAHP (■) during the 48 h incubation of *E. coli* aroB containing pKD130A and grown in M9 solution initially containing 56 mM D-glucose.
Figure 3:
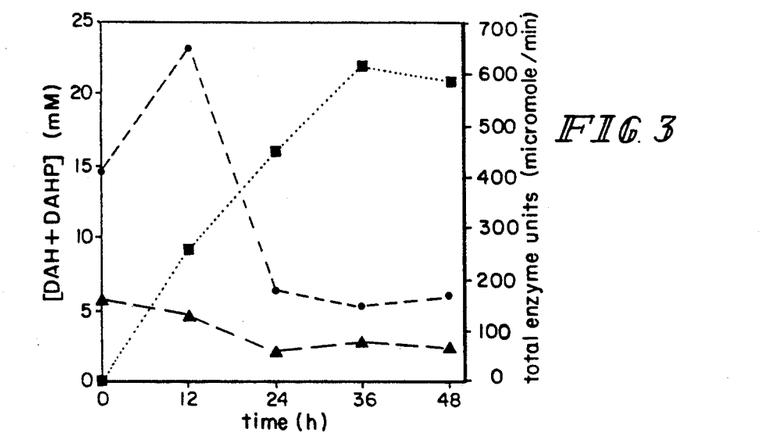
FIG. 3 shows the specific activities of DAHP synthase (●) and transketolase (▲) over the period of time during which DAH/DAHP (■) is synthesized by *E. coli* aroB (pKD130)

Determination of D-Glucose and DAH Concentrations and Transketolase/DAHP Synthase Specific Activities During *E. coli* BJ502 aroB (pKD130A) Synthesis of Heptulosonates (FIG. 2 and FIG. 3). Six 4 L Erlenmeyer flasks, each containing 1 L of LB with ampicillin, were inoculated (1% inoculant) with a fresh culture of BJ502 (pKD130A). Cells were grown at 37° C. for 9 hr, collected by centrifugation at 10000 g for 5 min at 4° C., and resuspended in six 4 L Erlenmeyer flasks containing 1 L M9 medium supplemented with glucose (10 g), shikimic acid and ampicillin. At timed intervals, all of the cells were harvested from one of the 4 L Erlenmeyer flasks by centrifugation at 10000 g for 5 min at 4° C. Glucose and DAH concentrations were determined in the resulting supernatant. The $H_1$ NMR analysis was used to quantitate the DAH levels. The pelleted cells were then evenly divided. One half of the cells were resuspended in 50 mM potassium phosphate buffer, pH 7.35, containing $MgCl_2$ (1 mM) and dithiothreitol (0.2 mM). Cells were disrupted by two passes through a French press at 18000 psi, cell debris removed by centrifugation at 25000 g for 30 min at 4° C., and transketolase activity determined. No purification was necessary to obtain linear rates of NADPH formation. The other half of the cells were resuspended in 50 mM potassium phosphate, pH 7, containing phosphoenolpyruvate (10 mM) and $CoCl_2$ (0.05 mM). Cells were disrupted by two passes through a French press at 18000 psi, cell debris removed by centrifugation at 25000 for 30 min at 4° C., and DAHP synthase activity determined as previously described.

RESULTS

Elaborating the role of transketolase in aromatic amino acid biosynthesis proceeded in several stages. Initially, the gene encoding the enzyme had to be isolated from an *E. coli* genomic library by complementation of an *E. coli* strain which possessed a mutation in the gene encoding transketolase. The nature of the selection scheme necessitated an appraisal of the enzyme product of the transketolase-encoding gene tkt. This entailed purification of transketolase to homogeneity from wild-type *E. coil* and comparison with the enzyme encoded by the isolated tkt. Transketolase-encoding tkt could then be exploited to vary the transketolase concentration in *E. coli* aroB. which lacks the enzyme dehydroquinate synthase and accumulates heptulosonates DAH and DAHP. Levels of heptulosonate accumulation served as a measure of the amount of carbon flow funneled into aromatic amino acid biosynthesis. In this fashion, the impact of variation in transketolase specific activity on the flow of carbon into the common pathway could be measured.

Isolation of a Transketolase-encoding Gene. Mutants of *Escherichia coli* completely void of transketolase activity have not been documented although strains resulting from chemical mutagenesis have been reported which have reduced transketolase levels. These "leaky" mutants are selected by virtue of a slow rate of growth in glucose-containing minimal medium lacking supplementation with aromatic amino acids or shikimic acid. Transketolase *E. coli* mutants are also unable to grow in medium where pentoses such as D-arabinose, D-ribose, or D-xylose are the exclusive source of carbon. *E. coli* BJ502, a strain derived from an *E. coli* K-12 variant possesses the leaky mutant phenotype presumed to typify diminished transketolase levels. *E. coli* BJ502 was determined to have approximately 15% of the units of transketolase activity found in unmutagenized wild-type *E. coli* K-12.

Complementation of *E. coli* BJ502 was used to probe an *E. coli* K-12 genomic library constructed in cosmid pLAFR3 from a partial BamHI digest of *E. coli* genomic DNA. Resistance to tetracycline provided the initial selection of transformants resulting from infection of *E. coli* BJ502 with the cosmid library packaged in phage lambda. Further selection for restored ability to grow on pentoses as the exclusive carbon source and normal growth rates on glucose lacking shikimate supplementation led to isolation of cosmid p10 which contained a 24 kb insert. Subcloning of p10 yielded plasmid pKD44B which contains a 5 kb insert capable of complementing the transketolase mutation in BJ502. A number of restriction enzyme digests of the pKD44B insert were prepared in order to reduce the length of complementing DNA even further. None of these subclones completely complemented BJ502 although partial complementation was achieved with a 3 kb BamHI, SalI fragment inserted into pBR322. Transformation of BJ502 with pBR322 containing the 3 kb insert restored growth on glucose medium lacking shikimate supplementation but transformants grew noticeably slower on pentose plates. Attention was therefore focused on the 5 kb BamHI insert of pKD44B.

Purification of Transketolase from *Escherichia coli*. Although complementation of *E. coli* BJ502 provides a criterion for isolation of the transketolase-encoding gene, potential ambiguities in the selection scheme were cause for concern. A variety of enzymes other than transketolase are required for growth on pentoses. Loss of any of these enzymes would lead to loss of ability to exploit pentoses as an exclusive pentose source. Furthermore, removal of the requirement for supplementation with shikimate was not a tight selection. *E. coli* BJ502 was capable of growth, albeit slow growth, in unsupplemented growth medium. This necessitated distinguishing between rates of growth as opposed to basing complementation on the presence or complete absence of colonies. Each of these weak points in the selection scheme could result in apparent complementation of *E. coli* BJ502 not stemming from restoration of normal levels of transketolase enzyme activity.

Corroboration for whether BJ502 complementing pKD44B encoded transketolase turned to enzymological evaluation with the purification of transketolase to homogeneity from wild-type *E. coli* K-12 and from *E. coli* BJ502(pKD44B). The continuous assays used to gauge transketolase activity relied on measured absorbance changes at $OD_{340}$ due to NADPH formation or NADH consumption. Neither of these assays could give a reliable measure of transketolase activity in crude cell lysates. Linear changes at $OD_{340}$ were observed only after purification by diethylaminoethyl cellulose (DE52) anion exchange chromatography. Integration of open column and HPLC anion exchange chromatography yielded homogeneous protein.

Gel electrophoresis indicated that the purified *E. coli* transketolase was homogeneous. Crosslinking of the purified transketolase with dimethyl suberimidate followed by gel electrophoresis under denaturing, reducing conditions with Coomassie Brilliant Blue visualization revealed that the enzyme was a homodimer having a subunit molecular weight of 72,500. Gel electrophoresis also indicated that purified genome-encoded (*E. coli* K-12) and plasmid-encoded (*E. coli* BJ502 (pKD44B)) transketolase comigrated. This comparison established that transketolase derived from the plasmid pKD44B has the same molecular weight and subunit composition as genome-encoded transketolase. Besides providing additional lines of evidence for successfully isolating a transketolase-encoding gene from the genomic library, protein gels demonstrated that the insert of pKD44B does not encode a significantly truncated version of the enzyme.

Introduction of aroB into the Host Genome and Genetic Variation of the In Vivo Specific Activities of Transketolase and DAHP Synthase. To minimize genome-based variations that might have an impact on flow of carbon into aromatic amino acid biosynthesis, E. coli BJ502 or E. coli BJ502 tkt+ aroB were used as the host strains for heptulosonate accumulations. E. coli BJ502 tkt+ aroB expressed wild-type levels of transketolase activity by virtue of P1 transduction of the tkt locus from E. coli RB791 into BJ502. The mutated locus encoding DHQ synthase was derived from E. coli JB5 a strain where aroB is closely linked to a transposon (Tn5) encoding kanamycin resistance which is inserted into the malT gene. Transduction with P1 was used to introduce the malT::Tn5 aroB locus into BJ502 and BJ502 tkt+.

E. coli strains, BJ502 aroB. BJ502 aroB tkt+, BJ502 aroB (pKD44B), BJ502 aroB (pKD112A), BJ502 aroB (pKD116B), BJ502 tkt+ aroB (pKD116B), and BJ502 aroB (pKD130A) gave transketolase specific activities, respectively, of 0.028, 0.17, 1.3, 1.5, 0.057, 0.18 and 1.4 units/mg. Transketolase specific activities above wild-type levels were achieved with localization of tkt in the low copy plasmid, pLAFR3. Insertion of tkt into the high copy plasmid, pBR325 also led to elevated levels of transketolase activity although the levels of expression were only marginally greater than those observed when tkt was localized in the low copy plasmid. The leaky mutation in the tkt locus of BJ502 provided transketolase specific activities below wild-type levels.

Variation in the concentration of DAHP synthase as measured by specific activity was realized with E. coli strains BJ502 aroB. BJ502 aroB (pKD272A), BJ502 aroB (pKD272B), BJ502 aroB (pKD116B), BJ502 aroB tkt+, BJ502 aroB tkt+ (pKD272A), BJ502 aroB tkt+ (pKD272B), and BJ502 aroB tkt+ (pKD116B). DAHP synthase activities were, respectively, 0.006, 0.11, 0.48, 3.18, 0.007, 0.14, 0.35, and 2.3 units/mg. Levels of DAHP synthase above wild-type levels were achieved with plasmid localization of aroB. Specific activity of DAHP synthase was strongly influenced by the copy number of the plasmid vector carrying aroF. The orientation of the aroF insert in the vector also had a significant impact on expression of DAHP synthase.

Figure 1:
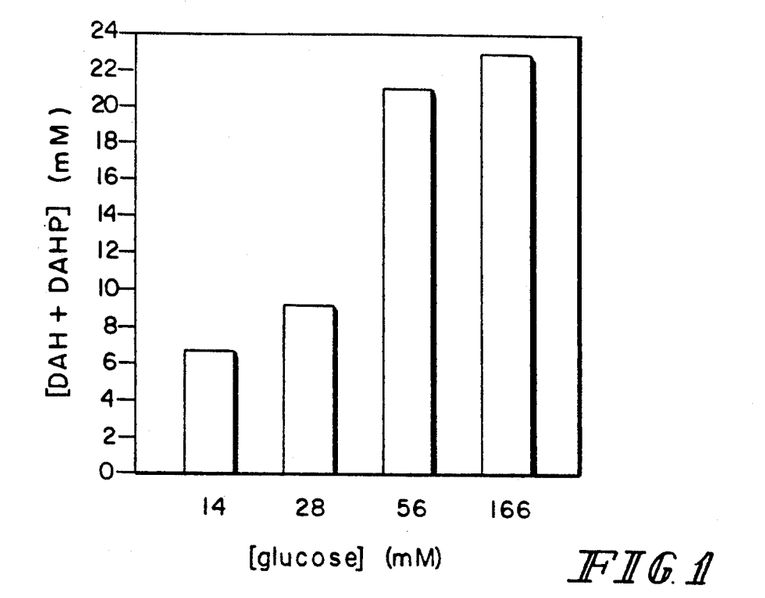
FIG. 1 illustrates changes in the concentration of DAH/DAHP synthesized by *E. coli* BJ502 (pKD130A) as a function of different concentrations of D-glucose in the culture medium.

Limitations on Whole Cell Synthesis of DAH and DAHP. A number of factors other than DAHP synthase and transketolase concentrations were examined as possible limitations to the levels of DAH and DAHP synthesized by E. coli aroB. To determine whether the culture medium's carbon source, D-glucose, might be a limiting factor BJ502 (pKD130A) was resuspended in minimal medium containing various concentrations of glucose. Heptulosonate synthesis was then quantitated by $^1$H NMR analysis of aliquots withdrawn from the accumulation supernatant. Resonances were integrated relative to an added standard. As depicted in FIG. 1, increasing the glucose concentration in the accumulation solution from its initial 14 mM concentration leads to an increase in the concentration of heptulosonates synthesized. A 21 mM level of heptulosonate synthesis is realized with 56 mM glucose. Increases in glucose concentration beyond 56 mM resulted in no significant improvement in heptulosonate synthesis. The time dependent decrease in glucose concentration relative to increases in heptulosonate concentration (FIG. 2) was also determined. While FIG. 2 suggests that glucose might be the limiting factor in heptulosonate accumulation, maintaining glucose concentrations between 28 mM and 56 mM throughout the accumulation period had no effect on the concentration of DAH synthesized. These results indicate that glucose concentration, once optimized, is not the limiting factor in DAH and DAHP synthesis assuming oxygen is not a limiting factor.

Instability of transketolase or DAHP synthase over the time course of the accumulation may also be a limitation on heptulosonate synthesis. To examine this possibility, BJ502 aroB (pKD130A) was resuspended in 56 mM glucose and total units of transketolase and DAHP synthase activity periodically measured along with determination of the levels of DAH and DAHP accumulating (FIG. 3). The total number of units of DAHP synthase activity after 36 hours is nearly 50% of its original value. At 36 hours, the total units of transketolase activity have declined but 50% of the original units of activity are still present. It thus appears that the complete cessation of DAH synthesis is not due to the loss of either DAHP synthase or transketolase. An increase in DAHP synthase units is observed during the first 12 hours of DAH accumulation. This is likely a consequence of the removal of transcriptional repression due to a decline in the intracellular concentrations of aromatic amino acids.

Direct evidence for transketolase determination of carbon flow into aromatic amino acid biosynthesis follows from the impact on DAH accumulation in E. coli aroB strains when the specific activities of transketolase and DAHP synthase are changed. Stepwise increases in DAHP synthase specific activity at depleted levels of transketolase resulted (FIG. 4) in only a modest increase in the carbon flow into the common pathway of aromatic amino acid biosynthesis in E. coli aroB. This indicates that DAHP synthase activity does not solely determine the rate of carbon flow into aromatic amino acid biosynthesis and that the carbon flow is strongly influenced by the availability of D-erythrose 4-phosphate as determined by transketolase activity. Increasing the availability of D-erythrose 4-phosphate by increasing transketolase activity leads to a large increase in carbon flow into the common pathway with increasing DAHP synthase levels (FIG. 4).

Figure 5:
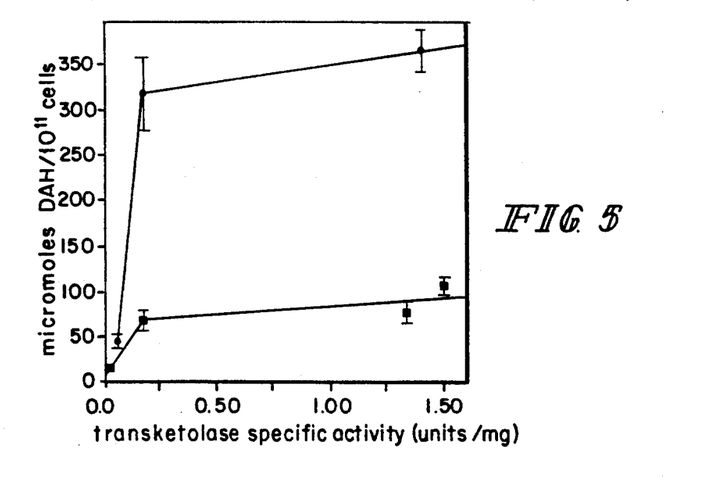
FIG. 5 shows the impact on DAH/DAHP synthesis resulting from incremental increases in transketolase activity at wild-type DAHP synthase levels (■) and elevated, plasmid encoded DAHP synthase levels (●).

The impact of transketolase on carbon flow into aromatic amino acid biosynthesis suggests that the in vivo concentrations of both transketolase and DAHP synthase should be increased to achieve the highest possible concentrations of heptulosonate synthesis by E. coli aroB. This results in a large quantity of carbon derived from the pentose phosphate pathway being siphoned into aromatic amino acid biosynthesis by the presence of pKD130A in E. coli BJ502 aroB. At the end of the accumulation, enzyme assay (FIG. 2) of the supernatant indicates that E. coli BJ502 aroB (pKD130A) has completely consumed the 56 mM concentration of glucose initially present in the culture medium. Analysis (FIG. 5) with $^1$H NMR of an aliquot removed from the supernatant confirms that the glucose has been completely removed. Based on the $^1$H NMR, a 21 mM concentration of DAH has been synthesized. This corresponds to channelling 44% of the carbon consumed by E. coli BJ502 aroB (pKD130A) into aromatic amino acid biosynthesis (56 mM D-glucose = 336 mM carbon, 21 mM DAH = 147 mM carbon).

Application of pKD130A to the synthesis of substrates of other enzymes intermediate in aromatic amino acid biosynthesis is also possible. A general characteristic of mutants lacking enzymes in aromatic amino acid biosynthesis is the accumulation in the growth supernatant of the missing enzyme's substrate. By changing the mutation in the host *E. coli* strain, introduction of pKD130A and the surge of carbon flow it creates could lead to whole cell synthesis of elevated levels of potentially any of the enzyme substrates of the common pathway of aromatic amino acid biosynthesis.

EXAMPLE 2

To determine the consequences of removing the rate limiting character of 3-dehydroquinate synthase (DHQ synthase), the aroB gene encoding that enzyme was inserted into plasmid pKD130A. A 1.65 kb fragment containing the aroB locus was introduced into the SphI site of plasmid pKD130A to produce pK3136. Plasmid pKD136 was transformed into *E. coli* AB2834 aroE. Analysis of the culture medium of AB2834 aroE (pKD136) indicated that 56 mM of glucose was converted into 30 mM DHS. Increasing the concentration of DHQ synthase results in exclusive synthesis of the substrate of the enzyme which is catalytically inactive. Based on the complete removal of D-glucose from the culture medium and the concentration of synthesized 3-dehydroshikimate (DHS), 54% of the carbon consumed by *E. coli* aroE (pKD136) has been siphoned into aromatic amino acid biosynthesis.

Plasmid pKD112A carried in *E. coli* strain DH5α and plasmid pKD130A carried in *E. coli* strain BJ502 aroB were deposited with the American Type Culture Collection in Rockville, Md., U.S.A. 20852, on Feb. 5, 1991, and assigned Accession Numbers ATCC 68525 and ATCC 68526, respectively.

Although the invention has been described in detail with reference to certain preferred embodiments, variations and modifications exist within the scope and spirit of the invention as described and defined in the following claims.

I claim:

1. Plasmid pKD112A.
2. Plasmid pKD130A.
3. A genetic element comprising a tkt gene and a gene selected from the group consisting of an aroF gene and an aroB gene.
4. DNA comprising a vector carrying a gene coding for transketolase.
5. The DNA of claim 4 wherein the vector is plasmid pBR325.
6. DNA of claim 5 further comprising a gene coding for DAHP synthase.
7. DNA of claim 6 wherein the gene coding for transketolase and the gene coding for DAHP synthase are carried on plasmid pKD130A.
8. A method for increasing carbon flow into the common aromatic pathway of a host cell comprising the step of transforming the host cell with recombinant DNA comprising a tkt gene so that transketolase is expressed at enhanced levels relative to wild type host cells.
9. The method of claim 8 further comprising the step of transferring into the host cell a gene selected from the group consisting of genes coding for enzymes catalyzing reactions in the common aromatic pathway.
10. The method of claim 9 wherein the gene codes for DAHP synthase or DHQ synthase.
11. The method of claim 10 wherein the gene is aroF or aroB.
12. The method of claim 8 wherein the host cell is a strain of *E. coli*.
13. The method of claim 12 wherein the strain of *E. coli* is BJ502 aroB.
14. A method for enhancing a host cell's biosynthetic production of compounds derived from the common aromatic pathway, said method comprising the step of increasing expression of transketolase in the host cell relative to a wild type host cell.
15. The method of claim 14 wherein the step of increasing expression of transketolase comprises transferring into the host cell a tkt gene.
16. A method for enhancing a host cell's biosynthetic production of compounds derived from the common aromatic pathway relative to wild type host cell's biosynthetic production of such compound, said method comprising the step of increasing expression in a host cell of a protein catalyzing conversion of D-fructose 6-phosphate to erythrose 4-phosphate.
17. The method of claim 16 wherein the step of increasing expression comprises transferring into the host cell a tkt gene.
18. The method of claim 16 further comprising the step of increasing expression in the host cell of a protein catalyzing reactions in the common aromatic pathway.
19. The method of claim 18, wherein the protein exhibits DAHP synthase activity or DHQ synthase activity.

* * * * *